United States Patent [19]
Vihko

[11] Patent Number: 6,140,468
[45] Date of Patent: Oct. 31, 2000

[54] RECOMBINANT HUMAN PROSTATE SPECIFIC ANTIGEN

[75] Inventor: Pirkko Vihko, Oulu, Finland

[73] Assignee: Boehringer Mannheim GmbH, Germany

[21] Appl. No.: 08/973,719

[22] PCT Filed: Jun. 26, 1996

[86] PCT No.: PCT/EP96/02779

§ 371 Date: Dec. 29, 1997

§ 102(e) Date: Dec. 29, 1997

[87] PCT Pub. No.: WO97/02350

PCT Pub. Date: Jan. 23, 1997

[30] Foreign Application Priority Data

Jun. 30, 1995 [FI] Finland ................................. 953257

[51] Int. Cl.$^7$ .................................................. C07K 14/00
[52] U.S. Cl. ...................... 530/350; 536/23.5; 435/348; 435/69.1; 435/70.1; 435/70.3; 530/416; 530/417
[58] Field of Search .......................... 536/23.5; 435/69.1, 435/70.1, 70.3, 348; 530/324, 412, 417, 350, 416

[56] References Cited

PUBLICATIONS

Ausubel et al. Current Protocols in Molecular Biology. Unit 16.8 "Expression of proteins in insect cells using baculoviral vectors" pp. 16.8.1–16.11.7, 1990.

Bei et al. "Generation, purification, and characterization of a recombinant source of human prostate–specific antigen" Journal of Clinical Laboratory Analysis. Vol. 9, pp. 261–268, Jan. 1, 1995.

Henttu et al. "cDNA coding for the entire human prostate specific antigen shows high homologies to the human tissue kallikrein genes" Biochem. and Biophys. Res. Commun. vol. 160. No. 2. pp. 903–910, Apr. 28, 1989.

Lundwall et al. "Molecular cloning of human prostate specific antigen cDNA" Febs Letters. vol. 214. No. 2, pp. 317–322, Apr. 1987.

Medin et al. "Efficient, low–cost protein factories: Expresssion of human adenosine deaminase in baculovirus–infected insect larvae" PNAS. vol. 87. pp. 2760–2764, Apr. 1990.

*Primary Examiner*—Julie Burke
*Assistant Examiner*—Larry R Helms
*Attorney, Agent, or Firm*—Arent, Fox, Kintner, Plotkin & Kahn

[57] ABSTRACT

The present invention relates to the production and purification of human prostate specific antigen (hPSA) by recombinant-DNA-technology. hPSA was produced in an active form by the baculovirus expression vector system. Recombinant protein was secreted into the culture medium at a high yield by infected cells and purified to homogeneity by three-step procedure containing cation-exchange chromatography and gel filtration. The active protein obtained differs from the native protein in that it is unglycosylated and that it does not degrade the kallikrein-specific substrate H-D-Pro-Phe-Arg-pNA.HCl. The inactive form of hPSA obtained has two additional amino acid residues in its N-terminus, and it does not form complexes. Possible uses of the recombinant protein are also disclosed.

3 Claims, 6 Drawing Sheets

SEQUENCE LISTING

```
<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Ser Arg Ile Val Gly Gly Trp Glu Cys Glu Lys His Ser
 1               5                  10
```

RECOMBINANT HUMAN PROSTATE SPECIFIC ANTIGEN

This application is a 35 U.S.C. 371 national stage filing of international application PCT/EP96/02779, filed Jun. 26, 1996.

The present invention relates to the production and purification of human prostate specific antigen (hPSA) by recombinant-DNA-technology, and the active and inactive protein forms obtained, as well as uses thereof.

Human prostate specific antigen (hPSA) is a 30–34 kDa single chain glycoprotein synthesized in the epithelial cells of the prostate gland and secreted into seminal fluid occurring at levels of 0.5–2 mg/ml.[1-3] hPSA is a potent proteolytic enzyme belonging to the group of extracellular serine proteases and has some features common with chymotrypsin-like enzymes.[4,5] According to the primary structure of hPSA it belongs to the human kallikrein family of proteases.[5,6] The two other members of this family are the human pancreatic/renal kallikrein and the human glandular kallikrein-1 (hGK-1). The hGK-1 is most closely related to hPSA having ≈80% sequence identity and is also expressed in human prostate tissue.[6-10]

Since Papsidero and colleagues[11] demonstrated that hPSA can be regularly detected in sera of prostatic cancer patients various commercial hPSA assays were developed using monoclonal or polyclonal antibodies, such as radio-immunoassay (RIA), enzyme-linked immunosorbent assay (ELISA), sandwich immunoassays and fluorescent immunoassays.[12] The clinical use of serum hPSA measurements have become the most central in the diagnosis and follow-up of treatment or prostatic cancer.[13,14] Because serum hPSA concentrations are also increased in patients with benign prostatic hyperplasia and in inflammatory conditions affecting the prostate, hPSA measurements alone are not sufficient screening tool for undiagnostised prostatic cancer. However, by combining serum hPSA concentrations to other methods as digital rectal examination and transrectal ultrasound the early diagnosing of prostatic cancer is improved.[15-17]

The recent findings have shown that hPSA can perhaps no longer be considered an absolutely prostate tissue-specific marker. Using immunohistochemical methods hPSA could be detected in female periurethral glands, apocrine sweat glands, apocrine breast cancers, salivary gland neoplasma and male urethra.[18] hPSA is also found in very low concentrations in human breast milk.[19]

In the serum the proteolytic activity of hPSA is inhibited by the formation of irreversible complexes with serum protease inhibitors such as $\alpha_1$-antichymotrypsin and $\alpha_2$-macroglobulin.[20-23] However, uncomplexed forms of hPSA also exist in bloodstream. The free form of hPSA and the form complexed with $\alpha_1$-antichymotrypsin are detected immunologically whereas $\alpha_2$-macroglobulin encapsulates the reactive hPSA epitopes in such a way that complexes are not quantifiable immunologically by conventional two-site immunometric assays.[24] Because of the complexity of the hPSA molecule and anti-hPSA antibodies, there is currently no internationally standardized method for the quantification of serum hPSA. Also it will be important to have consensus on what form of hPSA clinical assays should measure, the free, $\alpha_2$-macroglobulin bound, $\alpha_1$-antichymotrypsin bound or combinations of these forms of hPSA. But before any standardization of hPSA assay can be done a common standard is urgently required.

In the present work hPSA was produced as a recombinant protein in insect cells. The active form of hPSA was separated from the inactive form, and these were purified and characterized. Both of the protein forms were found to be suitable for use as a standard protein in hPSA assays, and also as an antigen in the preparation of very specific antibodies against hPSA.

In the present application we describe for the first time the development of an efficient expression system for hPSA by recombinant baculovirus-infected Sf9 insect cells.

The recombinant hPSA was secreted into the culture medium both in an active and an inactive form which were able to be separated in the last purification step with cation exchange chromatography. In the active form the signal and activation peptides were properly cleaved, as confirmed by N-terminal peptide sequencing.

The mature hPSA consists of a single chain polypeptide of 237 amino acids with a molecular weight ($M_r$) of 26079 for the peptide moiety of the molecule and contains a single N-linked carbohydrate side chain attached to asparagine-45.[6,34] It has been reported that when analyzing hPSA purified from seminal fluid by ion spray mass spectrometry (ISMS) the average $M_r$ of 28430 was detected indicating that the protein contains a carbohydrate residue of $M_r$ 2351.[35]

Analysis of the active recombinant hPSA by ISMS showed a $M_r$ of 26500 which indicates almost total absence of N-terminal sugars. Deglycosylation studies also confirmed the finding that the recombinant hPSA was not glycosylated. After N-glycosidase F or O-glycosidase treatment no detectable reduction in the molecular weight of 31 kDa of recombinant hPSA could be seen in SDS-PAGE analysis whereas the molecular weight of commercial hPSA reduced after N-glycosidase F treatment from 34 to 31 kDa. Despite the differences in the glycosylation of commercial and recombinant hPSAs they both were recognized in the fluoroimmunoassay by two mouse monoclonal antibodies.

In the native PAGE and isoelectric focusing our recombinant hPSA was shown to be more homogeneous than the commercial one. The commercial hPSA had five different forms in silver-stained native PAGE whereas recombinant hPSA had only one. In the isoelectric focusing the commercial hPSA had several isoforms with isoelectric points in the range pH 6.0 to 7.0 whereas the recombinant hPSA had one major pI of 7.7 and smaller one of 7.4. The specific activities of recombinant and commercial hPSAs were similar and comparable to the previously measured values when synthetic peptide substrate was used.[20]

The active form of the recombinant hPSA forms stable complexes with $\alpha_1$-antichymotrypsin and $\alpha_2$-macroglobulin in the similar manner as the commercial hPSA. $\alpha_1$-antichymotrypsin forms complexes of approximately 80 kDa and inactivates both hPSAs by binding to the active site of the protein.[20] It is known that $\alpha_2$-macroglobulin encapsulates the antigenic epitopes of hPSA in such a way that the protein escapes immunodetection in native conditions. Reducing SDS-PAGE of $\alpha_2$-macroglobulin-proteinase complexes produces $\alpha_2$-macroglobulin-fragments which have a molecular weight of approximately 85 kDa.[36] When recombinant hPSA (31 kDa) or commercial hPSA (34 kDa) were covalently bound to these fragments of $\alpha_2$-macroglobulin weak bands of approximately 110 kDa could be detected in immunoblots. Using small synthetic peptide substrates the chromogenic activities of the recombinant and commercial hPSAs increased immediately after $\alpha_2$-macroglobulin addition.

The inactive form of recombinant hPSA has two additional amino acid residues in its N-terminus. The N-terminal amino acid sequence thereof is Ser-Arg-Ile-Val-Gly-Gly-Trp-Glu-Cys-Glu-Lys-His-Ser (SEQ ID NO:1). This protein does not form complexes with $\alpha_1$-antichymotrypsin or $\alpha_2$-macroglobulin, and it has no activity on either on MeO-Suc-Arg-Pro-Tyr-pNA.HCl or H-D-Pro-Phe-Arg-pNA.2HCl substrates.

Having the recombinant hPSA we can avoid the contamination of hPSA with very similar hGK-1 protein. As these two proteins are expected to be identical in size and also share significant similarity in hydrophilic areas, they may be predicted to manifest extensive immunological cross-reactivity. We have also produced in insect cells the recombinant hGK-1 which is also recognized in the hPSA fluoroimmunoassay. Due to that we conclude that it is very important to use recombinant hPSA in the standardization of PSA-assay either as a standard protein or as an antigen in the preparation of proper antibodies against hPSA.

Antibodies can either be monoclonal or polyclonal antibodies which are raised against either the active or the inactive form of the recombinant hPSA of the invention. The antibodies can be produced by various processes known in the art, depending on the type of the antibody desired. To obtain polyclonal antibodies, a vertebrate, e.g. a rabbit is hyperimmunized with the antigen, blood is collected after repeated immunizations and the gamma globulin is isolated. Suitable processes for preparing of polyclonal antibodies are disclosed e.g. in Harlow and Lane, Eds., Antibodies, a laboratory manual, 1988 Cold Spring Harbor Press. To obtain monoclonal antibodies a small animal, typically a mouse or a rat, is immunized with the antigen, the spleen or popliteal lymph node is removed, and the lymphocytes are combined with myeloma cells in the presence of a suitable fusion promoter. The hybrid cells so obtained, called hybridomas, are screened to isolate individual clones each of which secretes one unique antibody to the antigen. A general method for obtaining monoclonal antibodies was described by Kohler and Milstein in Nature 256:495–497 (1975).

EXPERIMENTAL

Construction of the Recombinant Plasmid Transfer Vector

The hPSA-cDNA (1464 bp) was cloned into EcoRI site of the pVL1392 nonfusion transfer vector (Invitrogen) and introduced with homologous recombination into the genome of *Autografa californica* nuclear polyhedrosis virus (AcNPV).

Generation of the Recombinant Baculovirus and Protein Production

Recombinant virus containing the hPSA DNA fragment, was used to infect *Spodoptera frugiperda* (Sf9) cells (ATCC CRL1711). Recombinant protein was produced using exponentially growing Sf9 insect cells ($2 \times 10^6$/ml) at 27° C. infected by hPSA-AcNPV at a multiplicity of infection 1 in 1000 ml spinner flasks (Bellco) containing 10% FCS in complete TNM-FH insect medium (Sigma) with antibiotics. For harvesting the cells were centrifuged and the supernatant was collected and stored for further purification of the recombinant hPSA. The amount of hPSA secreted into the culture medium was determined by time-resolved fluoroimmunoassay kit (DELFIA, Wallac).

Expression of hPSA in Sf9 Cells

The recombinant hPSA was overproduced in Sf9 cells. The protein was secreted into the culture medium and the production reached a maximum at 4 days after infection being 3–4 mg/liter. Scaling-up of Sf9 insect cell cultures was effected using the following series: T-flasks, spinner bottles, 2-liter bioreactor and 30-liter bioreactor.

Purification of Recombinant hPSA

The harvested medium from the recombinant virus infection was concentrated with a Pellicon cassette system (cut-off, 10 kDa; Millipore) and dialyzed in 50 mM sodium acetate buffer (pH 6.8). The concentrate was then loaded onto a fluidized bed column (Streamline 50, 5×100 cm, 100 ml/min) containing strong cation-exchange matrix (600 ml, Streamline SP, Pharmacia). After washing the recombinant hPSA was eluted from the column with linear salt gradient from 0 to 0.25 M NaCl. The fractions reacting with rabbit anti-hPSA serum (slot-blot) were concentrated (Amicon) for gel filtration chromatography with Sephacryl S-200 (2.6×80 cm, 0.7 ml/min, Pharmacia) column eluted with 50 mM sodium phosphate buffer (pH 7.0) containing 0.15 M NaCl. The fractions with the highest hPSA content were pooled and dialyzed in 50 mM sodium phosphate buffer (pH 5.8) for cation-exchange chromatography with Mono-S column (0.5×5 cm, 0.5 ml/min, Pharmacia). The active (90–110 mM) and inactive (120–140 mM) pools of recombinant hPSA were eluted from the column with a linear salt gradient of NaCl. The Streamline 50 and the Sephacryl S-200 columns were connected to BioPilot and the Mono-S column to FPLC automated chromatography systems (Pharmacia).

The purification procedure is illustrated in Scheme I.

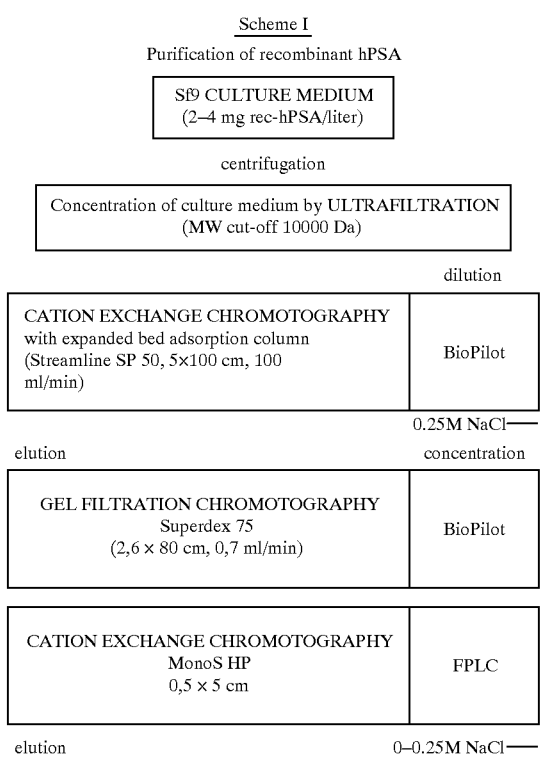

Figure 6:
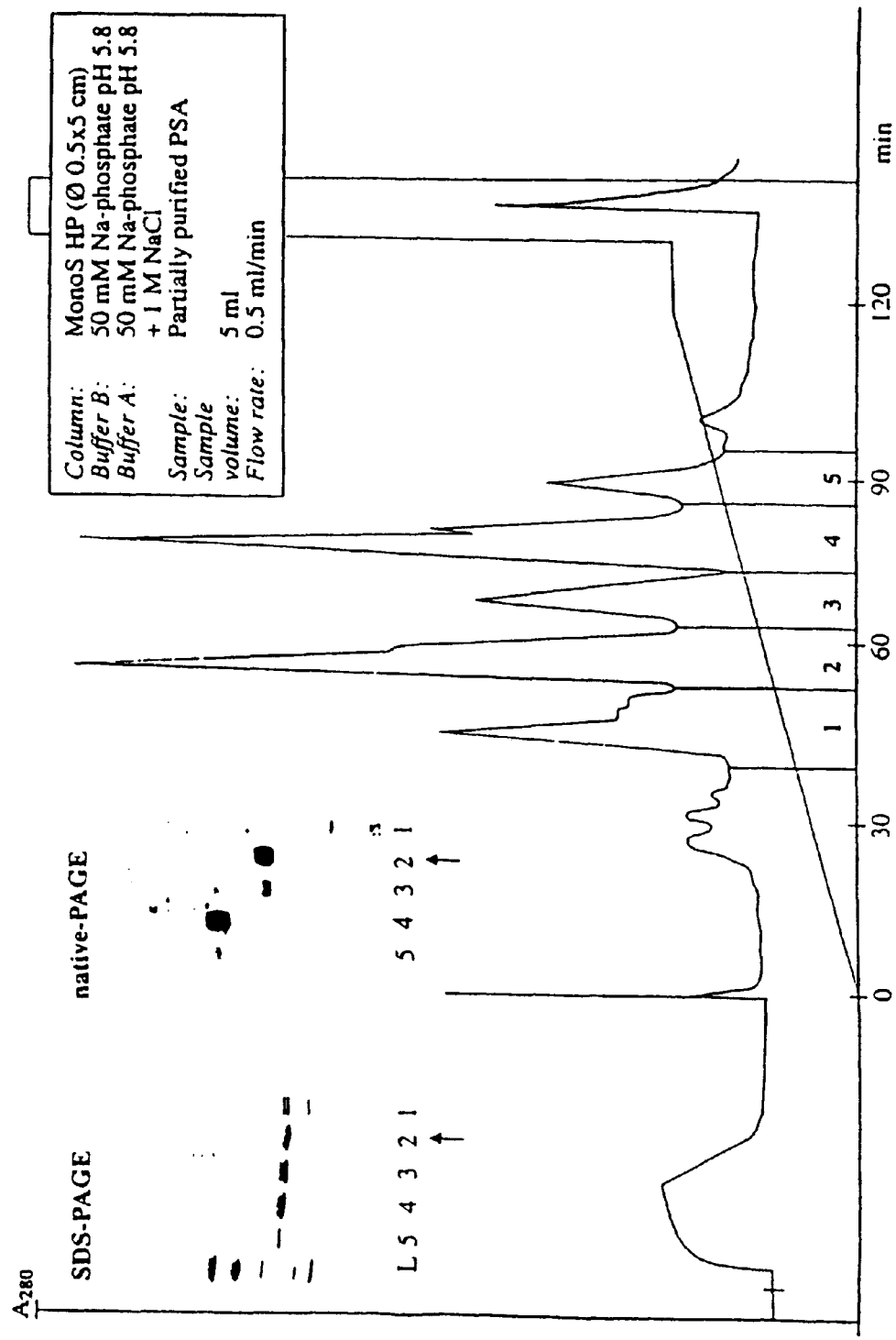
FIG. 6: The last purification step of recombinant hPSA with cation exchange chromatography. Elution with linear sodium chloride gradient. Active rec-hPSA: peak 2. Inactive rec-hPSA: peak 5. Peaks 3 and 4 contain the mixture of both forms.

The active and inactive forms of recombinant hPSA were obtained in purity (FIG. 6).

Characterization of Recombinant hPSA

Figure 1:
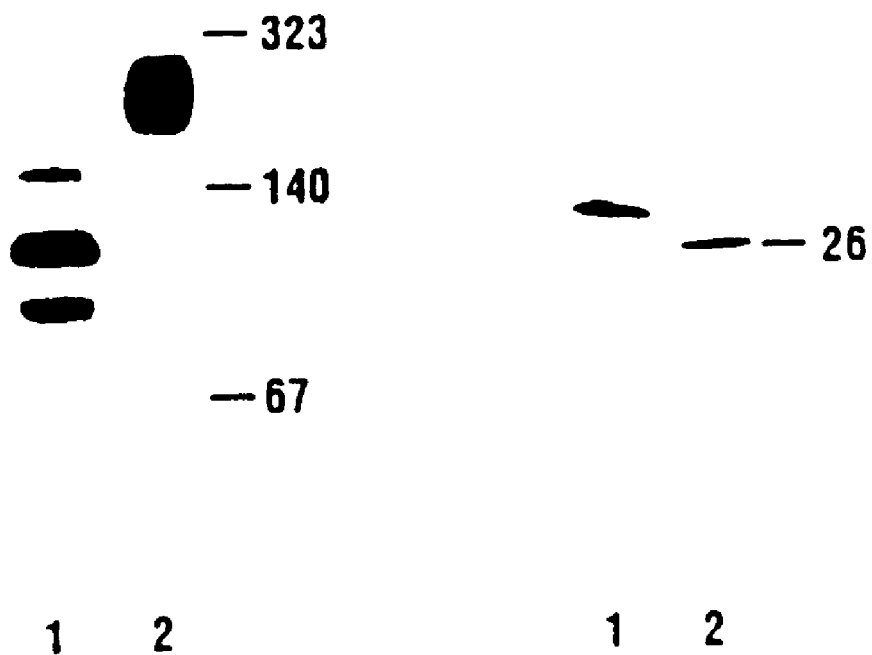
FIGS. 1A and 1B: Silver-stained native (A.) and reduced SDS (B.) polyacrylamide gel electrophoresis of the commercial hPSA purified from seminal fluid (Line 1) and the recombinant hPSA (active form) (Line 2)
Figure 2:
FIG. 2: Silver-stained isoelectric focusing of the recombinant hPSA (active form) (Line 1) and commercial hPSA (Line 2)
Figure 2:

The recombinant hPSA was produced into culture medium in two forms, active and inactive, which were able to be separated in the last purification step with cation-exchange chromatography. The active form of hPSA was eluted with lower salt concentration than the inactive one. The specific activity of the pure protein was 73 nmol×min$^{-1}$×mg$^{-1}$ with the synthetic peptide MeO-Suc-Arg-Pro-Tyr-pNA.HCl as the substrate. The specific activity for commercial hPSA was 79 nmol×min$^{-1}$×mg$^{-1}$. Purified active recombinant hPSA was present in silver-stained SDS-PAGE in one band of 26 kDa and the commercial hPSA purified from seminal fluid had one band of 34 kDa (FIG. 1B). in the silver-stained native PAGE the active recombinant hPSA showed one band of 200 kDa whereas hPSA from seminal fluid had four bands between 70 and 150 kDa (FIG. 1A). All these forms of recombinant and commercial hPSAs were recognized in Western blottings of SDS-PAGE and native PAGE with the rabbit polyclonal antibody raised against hPSA purified from seminal fluid. In the immunoblot of the native PAGE there can be seen one additional band in the sample of recombinant hPSA and three in commercial hPSA comparing to the silver-stained native PAGE of the same samples (FIG. 1A). Silver-stained isoelectric focusing (FIG. 2) shows the commercial hPSA to exist in several isoforms with isoelectric points in the pH range from 6.0 to 7.0. Our active recombinant hPSA showed one major band in the pH 7.7 and the smaller one in the pH 7.4. Both forms were recognized in the immunostaining of blotted IEF gel (data not shown).

Quantitative Recovery of Recombinant hPSA by Fluoroimmunoassay

The protein concentration of purified recombinant hPSA was measured by the method of Lowry et al. with bovine gamma globulin (Bio-Rad) as the standard.[25] The recovery of recombinant hPSA was further measured by time-resolved fluoroimmunoassay (DELFIA PSA kit, Wallac) which recognized both free PSA and complexed with $\alpha^1$-antichymotrypsin.[21, 22] For the assay the recombinant hPSA antigen was diluted with "zero" standard of fluoroimmunoassay kit containing human serum in Tris-HCl buffered salt solution (pH 7.8).

Figure 5:
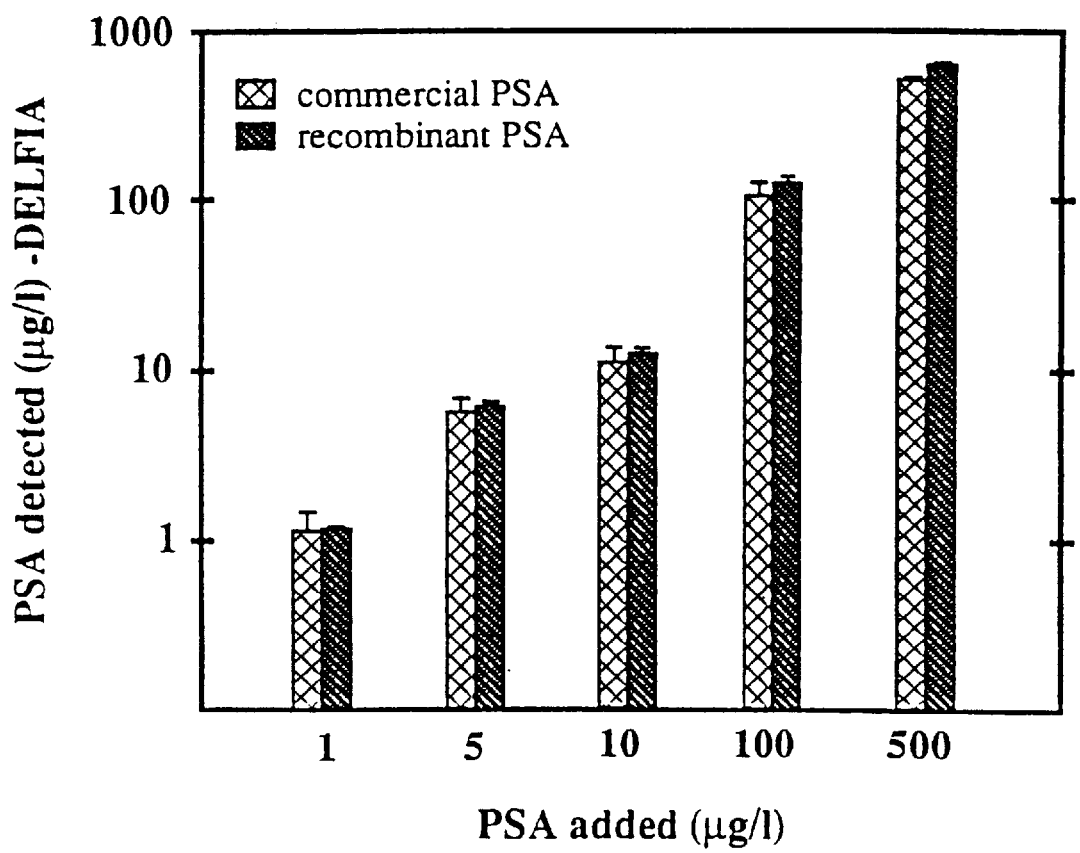
FIG. 5: Quantitative recovery of purified recombinant hPSA and commercial hPSA measured by time-resolved fluoroimmunoassay for hPSA Pure recombinant hPSA (active form) (●) and commercial hPSA (○) were diluted with human serum containing buffer to concentrations 1, 5, 10, 100, 500 µg/L. These concentrations were assayed in duplicate by fluoroimmunoassay kit (Wallac) for hPSA.—100% recovery.

The recombinant and commercial hPSAs were diluted with human serum containing buffer to yield concentrations of 1, 5, 10, 100 and 500 µg/L which were tested in duplicate for hPSA concentrations with fluoroimmunoassay. The recoveries of the recombinant and the commercial hPSAs were 119±3% (n=5) and 149+13% (n=5), respectively when compared with the hPSA calibrator in the fluoroimmunoassay kit (FIG. 5)

Separating of Active and Inactive Forms of Recombinant hPSA Produced

The last purification step of recombinant hPSA was done with cation exchange chromatography. With linear sodium chloride gradient we could separate the active form of hPSA in peak 2 from the inactive form in peak 5. Peaks 3 and 4 contained the mixture of both forms. (FIG. 6). The conditions were as follows.

Column: MonoS HP (Ø 0.5×5 cm)
Buffer B: 50 mM Na-phosphate, pH 5.8
Buffer A: 50 mM Na-phosphate, pH 5.8+1M NaCl
Sample: Partially purified rec-hPSA
Sample volume: 5 ml
Flow rate: 0.5 ml/min.

In silver stained native PAGE the active form of recombinant hPSA had the molecular weight of 195 kDa and the inactive form 370 kDa (not shown).

Gel Electrophoresis and Immunoblotting

The purity and characterization of recombinant hPSA were evaluated by SDS-PAGE and native PAGE. Both electrophoresis were carried out on a PhastSystem (Pharmacia) with PhastGel gradient media 10-15 for SDS-PAGE and 8-25 for native PAGE and were silver-stained.[26-30] In Western blotting, the proteins were transferred onto nitrocellulose membranes with PhastTransfer (Pharmacia).[31] Rabbit polyclonal antibody raised against hPSA purified from seminal fluid[32] was used together with a ProtoBlot AP system (Promega) to detect expressed protein. In all electrophoresis the recombinant hPSA was compared to the commercial hPSA purified from seminal fluid (Calbiochem). Isoelectric focusing was performed on a PhastSystem with PhastGel IEF media, pH range 3–9, and gels were silver-stained.

Formation of Complexes Between PSA and Proteinase Inhibitors

Reaction mixtures were prepared in which 10 μg of recombinant or commercial purified hPSAs were incubated with 40 μg of purified $\alpha_1$-antichymotrypsin (Calbiochem) or 200 μg of $\alpha_2$-macroglobulin (Calbiochem). All reactions were performed at 37° C. for different periods of time (0.1, 1, 15, 60 min) in 20 mM Tris buffer containing 150 mM NaCl (pH 7.4). Reaction mixtures were analysed by activity measurements and Western blotting of SDS-PAGE.

Figure 3:
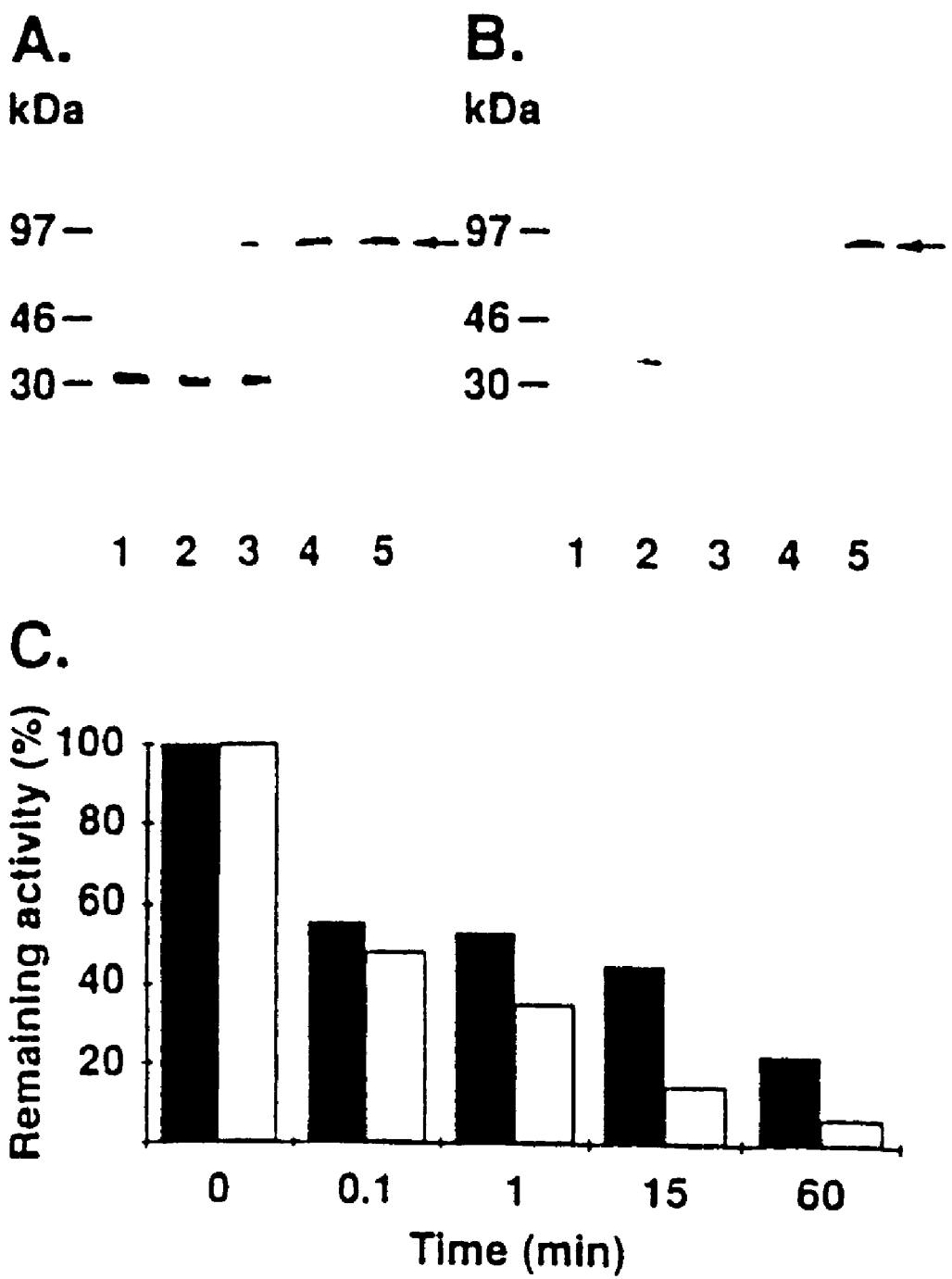
FIGS. 3A, 3B, and 3C: Interaction of recombinant and commercial hPSAs with $\alpha_1$-antichymotrypsin Formation of complexes with pure recombinant hPSA (active form) (A.) and with commercial hPSA (B.) was followed by Western blotting of SDS-PAGE. All samples were reduced with 5% 2-mercaptoethanol before analysis. Lines 2–5 show the time course of the interaction, incubation times were: (2) 0.1 min, (3) 1 min, (4) 15 min, (5) 60 min. Line A.1 is noncomplexed recombinant hPSA and Line B.1 noncomplexed commercial hPSA. The chromogenic activity of recombinant hPSA (□) and commercial hPSA (■) was followed during complex formation in part C.
Figure 4:
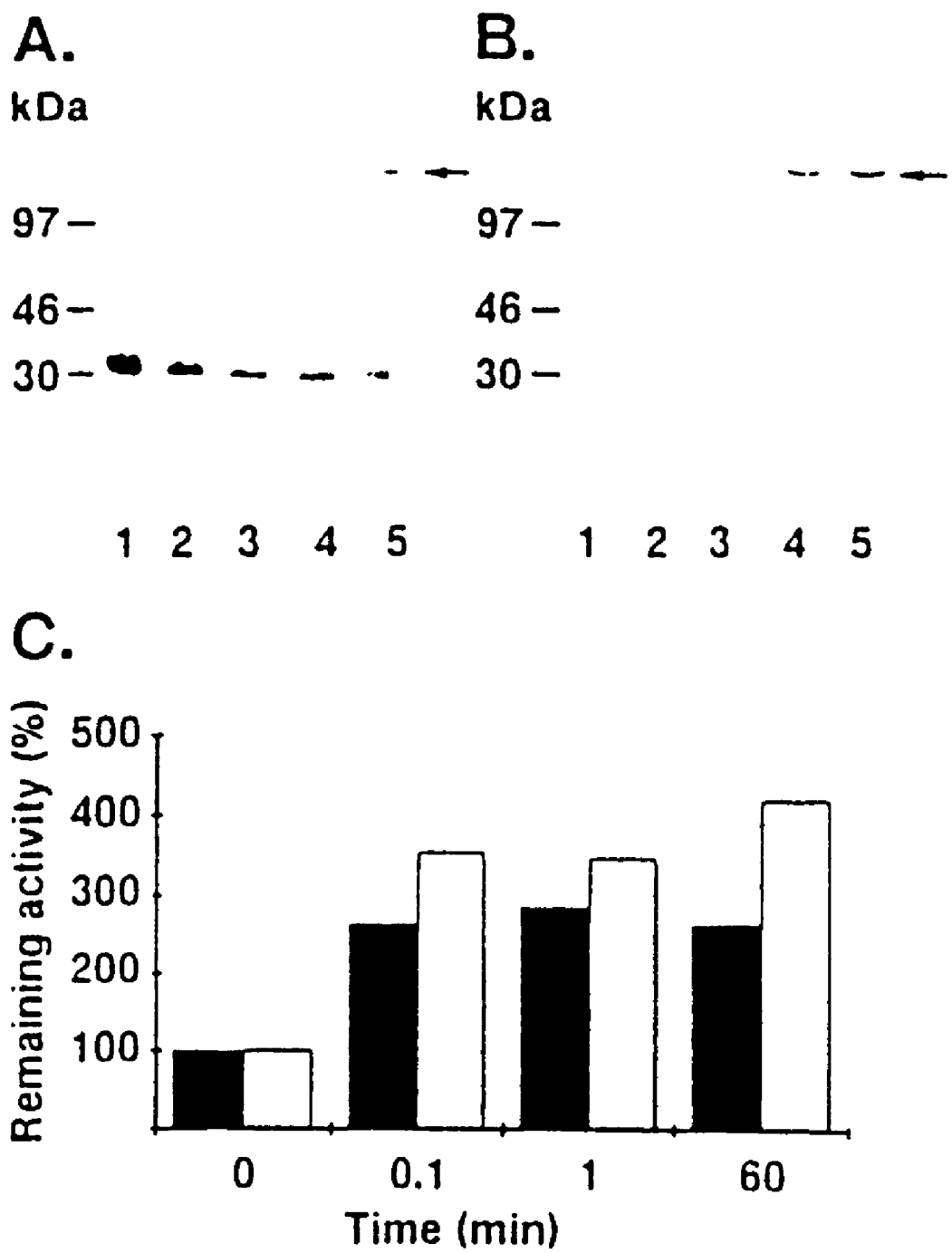
FIGS. 4A, 4B, and 4C: Interactions of recombinant and commercial hPSAs with $\alpha_2$-macroglobulin Formation of complexes with pure recombinant hPSA (active form) (A.) and with commercial hPSA (B.) was followed by Western blotting of SDS-PAGE. All samples were reduced with 5% 2-mercaptoethanol before analysis. Lines 2–5 show the time course of the interaction, incubation times were: (2) 0.1 min, (3) 1 min, (4) 15 min, (5) 60 min. Line A.1 is noncomplexed recombinant hPSA and Line B.1 noncomplexed commercial hPSA. The chromogenic activity of recombinant hPSA (□) and commercial hPSA (■) was followed during complex formation in part C.

The active form of our recombinant hPSA formed stable complexes in reduced SDS-PAGE with $\alpha_1$-antichymotrypsin and $\alpha_2$-macroglobulin as did commercial hPSA. After 1 min approximately 80 kDa band can be seen in Western blots when both hPSAs were complexed with $\alpha_1$-antichymotrypsin (a twofold molar excess of $\alpha_1$-antichymotrypsin) (FIGS. 3A, B). The loss of hPSA-mediated hydrolysis of MeO-Suc-Arg-Pro-Tyr-pNA.HCl was achieved immediately after complex formation begins (FIG. 3C). After 1 min 53% of recombinant hPSA and 35% of commercial hPSA activities were left. When adding $\alpha_2$-macroglobulin to the incubation mixtures containing commercial or our recombinant hPSAs (in a 1:1 molar ratio) the complex formation begins immediately and weak band of approximately 110 kDa can be seen in Western blots of SDS-PAGE (FIGS. 4 A, B). The addition of $\alpha_2$-macroglobulin increased the activities of both PSAs, threefold with recombinant hPSA and fourfold with the commercial hPSA (FIG. 4C).

Measurements of PSA Activity

PSA-hydrolysis of MeO-Suc-Arg-Pro-Tyr-pNA.HCl (Chromogenix AB) at a final concentration of 1 mM was measured at 405 nm. The reactions were performed at 37° C. and initiated by addition of the chromogenic substrate (50 μl) to 200 μl 50 mM Tris buffer (pH 7.8) with 100 mM NaCl containing hPSA (25 μg). After one hour the reaction was stopped by adding 800 μl 0.6 M acetic acid and the reaction rate (nmol pNA formed per min) was calculated from the standard curve of p-nitroaniline (pNA).

Enzymatic Deglycosylation of hPSA

Ten micrograms of recombinant (13 μl) and commercial (3 μl) hPSAs were mixed with 0.5 μl of 10% SDS, the total volumes were adjusted to 15 μl with 0.1 M sodium phosphate containing 25 mM EDTA (pH 7.2), and the mixtures were boiled for 3 min. After the pretreatment, 5 μl of 10% (vol/vol) Triton X-100, 3 μl N-glycosidase F solution (0.6 unit) or 5 μl O-glycosidase solution (2.5 milliunits) were added to the protein solutions (both enzyme solutions were purchased from Boehringer Mannheim). The final volume was adjusted to 30 μl with 0.1 M sodium phosphate buffer containing 25 mM EDTA (pH 7.2). The mixtures were incubated at 37° C. overnight and analyzed by SDS-PAGE under nonreducing conditions.

O-Glycosidase and N-glycosidase F did not have any detectable effects on the molecular mass of recombinant hPSA in SDS-PAGE whereas after deglycosylation of commercial hPSA with N-glycosidase F the reduction of 3 kDa in molecular weight can be seen.

References

1. Sensabaugh G F. Isolation and characterization of a semen-specific protein from human seminal plasma: A potential new marker for semen identification. *J Forensic Sci* 1978; 23:106–115.
2. Wang M C, Valenzuela L A, Murphy G P, Chu T M. Purification of human prostate specific antigen. *Invest Urol* 1979; 17: 159–163.
3. Wang M C, Papsidero L D, Kuriyama M, et al. Prostate antigen: A new potential marker for prostatic cancer. *The Prostate* 1981; 2: 89–96.
4. Hara M. Kimura H. Two prostate-specific antigens, γ-seminoprotein and β-microseminoprotein. *J Lab Clin Med* 1989; 113: 541–548.
5. Watt K W K, Lee P-J, Timkulu T M, et al. Human prostate-specific antigen: Structural and functional similarity with serine proteases. *Proc Natl Acad Sci USA* 1986; 83:3166–3170.
6. Lundwall A, Lilja H. Molecular cloning of human prostate specific antigen cDNA. *FEBS Lett* 1987; 214: 317–322.
7. Henttu P, Vihko P. cDNA coding for the entire human prostate specific antigen shows high homologies to the human tissue kallikrein genes. *Biochem Biophys Res Commun* 1989; 160: 903–910.
8. Schedlich L J, Bennets B H, Morris B J. Primary structure of a human glandular kallikrein gene. *DNA* 1978; 6: 429–437.
9. Chapdelaine P, Paradis G, Tremblay R R, Dube J. High level of expression in the prostate of a human glandular kallikrein mRNA related to prostate-specific antigen. *FEBS Lett* 1988; 236: 205–208.
10. Henttu P, Lukkarinen O, Vihko P. Expression of the gene coding for human prostate-specific antigen and related hGK-1 in benign and malignant tumors of the human prostate. *Int J Cancer* 1990; 45: 654–660.
11. Papsidero L D, Wang M C, Valenzuela L A, et al. A prostate antigen in sera of prostatic cancer patients. *Cancer Res* 1980; 40: 2428–2432.
12. Takayama T K, Vessella R L, Lange P H. A brief review of ultrasensitive prostate-specific antigen assays for the evaluation of patients after radical prostatectomy. *World J Urol* 1993; 11: 192–195.
13. Stamey T A, Yang N, Hay A R, et al. Prostate-specific antigen as a serum marker for adenocarcinoma of the prostate. *N Engl J Med* 1987; 317: 909–916.
14. Kablin J N. Prostate specific antigen: Clinical use in the diagnosis and management of prostate cancer. *Geriatrics* 1992; 47: 26–32.
15. Cooner W H, Mosley B R, Rutherford C L et al. Prostate cancer detection in a clinical urological practice by ultrasonography, digital rectal examination and prostate specific antigen. *J Urol* 1990; 143: 1146–1154.
16. Catalona W J, Smith D S, Ratliff T L et al. Measurement of prostate-specific antigen in serum as a screening test for prostate cancer. *N Engl J Med* 1991; 324: 1156–1161.
17. Partin A W, Oesterling J E. The clinical usefulness of prostate specific antigen: Update 1994. *J Urol* 1994; 152: 1358–1368.

18. Graves H C B. Nonprostatic sources of prostate-specific antigen: a steroid hormone-dependent phenomen. *Clin Chem* 1995; 41: 7–9.
19. Yu H, Diamandis E P. Prostate-specific antigen in milk of lactating women. *Clin Chem* 1995; 41: 54–58.
20. Christensson A. Laurell C-B. Lilja H. Enzymatic activity of prostate-specific antigen and its reactions with extracellular serine protease inhibitors. *E J Biochem* 1990; 104: 755–763.
21. Stenman U H, Leinonen J, Alfthan H, et al. A complex between prostate-specific antigen and $\alpha_1$-antichymotrypsin is the major form of prostate-specific antigen in serum of patients with prostatic cancer: assay of the complex improves clinical sensitivity for cancer. *Cancer Res* 1991; 51: 222–226.
22. Lilja H, Christensson A, Dahlen U, et al. Prostate-specific antigen in human serum occurs predominantly in complex with $\alpha_1$-antichymotrypsin. *Clin Chem* 1991; 37: 1618–1625.
23. Christensson A, Björk T, Nilsson O, et al. Serum prostate specific antigen complexed to $\alpha_1$-antichymotrypsin as an indicator of prostate cancer. *J Urol* 1993; 150: 100–105.
24. Zhou A M, Tewari P C, Bluestein B I, et al. Multiple forms of prostate-specific antigen in serum: differences in immunorecognition by monoclonal and polyclonal assays. *Clin Chem* 1993; 39: 2483–2491.
25. Lowry O H, Rosebrough N J, Farr A L, Randall R J. Protein measurement with the Folin phenol reagent. *J Biol Chem* 1951; 193: 265–275.
26. Jovin T M. Multiphasic zone electrophoresis. I. Steady-state moving boundary systems formed by different electrolyte combinations. *Biochem* 1973; 12: 871–890.
27. Wyckoff M, Rodbard D, Crambach A. Polyacrylamide gel electrophoresis in sodium dodecyl sulfate containing buffers using multiphasic buffer systems: Properties of the stack, valid Rf measurements and optimized procedure. *Anal Biochem* 1977; 78: 459482.
28. Davis B J. Disc Electrophoresis II: Methods and Application to human serum proteins. *Ann N Y Acad Sci* 1964; 121: 404–427.
29. Andrews A T. Molecular weight measurement and the use of gel concentration gradients. In Electrophoresis. Theory, Techniques and Biochemical and Clinical Applications, Peacoce A R, Harrington W F, eds. Clarendon Press, Oxford, 1981: 63–80.
30. Heukeshoven J, Dernick R. Simplified method for silver staining of proteins in polyacrylamide gels and the mechanism of silver staining. *Electrophoresis* 1985; 6: 103–112.
31. Prieur B, Russo-Marie F. An automated Western blot analysis using the Phast-System. *Anal Biochem* 1988; 172: 338–343.
32. Vihko P, Kurkela R, Ramberg J, et al. Time-resolved immunofluorometric assay of human prostate-specific antigen. *Clin Chem* 1990; 36: 92–95.
33. Schaller J, Akiyama K, Tsuda R, et al. Isolation, characterization and amino-acid sequence of γ-seminoprotein, a glycoprotein from human seminal plasma. *Eur J Biochem* 1987; 170: 111–120.
34. Bélanger As van Halbeek H, Graves H C B, et al. Molecular mass and carbohydrate structure of prostate specific antigen. In The Endocrine Society 76th Annual Meeting, Anaheim, Calif., Jun. 15–18, 1994: Abstract 493.
35. Petersen C M. $\alpha_2$-macroglobulin and pregnancy zone protein. *Danish Medical Bulletin* 1993; 40: 409–446.

I claim:

1. A recombinant human prostate specific antigen (hPSA) which is obtainable by recombinant DNA technology using a baculovirus expression system in infected insect cells, wherein the first thirteen N-terminal amino acids of said recombinant hPSA consists of Ser-Arg-Ile-Val-Gly-Gly-Trp-Glu-Cys-Glu-Lys-His-Ser (SEQ ID NO:1), does not form complexes with $\alpha_1$-antichymotrypsin or $\alpha_2$-macroglobulin and has no activity on the substrates MeO-Suc-Arg-Pro-Tyr-pNA.HCl and H-D-Pro-Phe-Arg-pNA.2HCl.

2. A process for the production of the recombinant hPSA according to claim 1, comprising the steps of a) incorporating a cDNA encoding hPSA into a transfer vector,
   b) cotransfecting said vector with baculovirus-DNA into *Spodoptera frugiperda* cells,
   c) cultivating said cells in an insect cell cultivation medium,
   d) harvesting the culture medium, and
   e) purifying the hPSA secreted into the culture medium.

3. The process according to claim 2 wherein said purifying step comprises dialyzing the culture medium to obtain a dialysate,
   loading the dialysate onto a fluidized bed column having a strong cation-exchange matrix, eluting any hPSA from the column using a salt gradient, concentrating the hPSA fragments to obtain a concentrate, purifying the obtained concentrate using a gel filtration column, dialyzing any hPSA fractions eluted from the gel filtration column to obtain a second dialyzate, loading the second dialyzate onto a cation-exchange chromatography column, and eluting any active and inactive pools of recombinant hPSA from the cation-exchange chromatography column with a linear salt gradient.

* * * * *